United States Patent [19]

Martin

[11] Patent Number: 5,646,197

[45] Date of Patent: Jul. 8, 1997

[54] ANTIMICROBIAL ROOT CANAL SEALER

[76] Inventor: Howard Martin, 1106 Spring St., Silver Spring, Md. 20910

[21] Appl. No.: 543,378

[22] Filed: Oct. 16, 1995

[51] Int. Cl.$^6$ ...................................................... A61K 6/08
[52] U.S. Cl. .......................... 523/118; 523/117; 524/432; 524/462; 524/408; 524/798; 433/228.1; 106/35
[58] Field of Search ...................................... 523/117, 118; 524/432, 462, 408, 798; 433/228.1; 106/35

[56] References Cited

U.S. PATENT DOCUMENTS

| | | | |
|---|---|---|---|
| 3,808,686 | 5/1974 | Tauman et al. | 433/167 |
| 4,083,955 | 4/1978 | Grabenstetter et al. | 424/52 |
| 4,309,409 | 1/1982 | Coll-Palagos et al. | 424/52 |
| 4,652,593 | 3/1987 | Kawahara et al. | 523/117 |
| 4,657,592 | 4/1987 | Takubo | 106/35 |
| 4,931,096 | 6/1990 | Fujisawa et al. | 523/113 |
| 5,342,441 | 8/1994 | Mandai et al. | 106/35 |

*Primary Examiner*—Andrew E. C. Merriam
*Attorney, Agent, or Firm*—Walter G. Finch

[57] ABSTRACT

The present invention is directed to a root canal sealer which satisfies the need for obtaining a tight seal. The root canal sealer comprises the following powders in the following weight ratios: 31 to 41% zinc oxide, 25% hydrogenated rosin glycerol ester (staybelite resin), 10% bismuth subcarbonate, 10% barium sulfate, 1% anhydrous sodium borate, and 5–15% triiodomethane. The powders are mixed with 100% eugenol to form a creamy paste.

1 Claim, No Drawings

ANTIMICROBIAL ROOT CANAL SEALER

BACKGROUND

The function of root canal fillings is to completely seal the prepared root canal to prevent infection of the surrounding tissue and possible failure of the root canal. The goal is to obtain as tight a seal as possible and to block off all openings through which infection could occur. The better the seal, the better the prognosis for the root canal.

Root canal sealers or cements are used in conjunction with gutta percha solid cores to achieve the best seal possible of the root canal. The root canal sealer is inserted into the canal first and the gutta percha cone is used to force the root canal sealer into the space between the root canal wall and the gutta percha and effectively fill canal irregularities.

However, as there is no adhesion between the root canal sealer and the gutta percha cone and the adhesion between the root canal sealer and root canal wall is incomplete, percolation of tissue fluids, saliva and bacteria in this space is possible. This percolation of fluids and bacteria will likely lead to infection and subsequent failure of the root canal.

A majority of the root canal sealers available today use zinc oxide as the main ingredient with varying degrees of different components to make up the powder. This powder is mixed with a liquid, usually eugenol, until a creamy mixture results. This mixture is then inserted into the root canal.

The problem appears to be with the zinc oxide component. It is inflammatory and cytotoxic to the surrounding tissue. This causes pain, bacterial attraction, and delayed healing. Therefore, lowering the zinc oxide content of the root canal sealer would alleviate some of the cytotoxic and inflammatory effects.

Several root canal sealers having a variety of zinc oxide based formulations have been used in the past. However, many of these sealers set quickly and provide inadequate working time for the dentist. Some sealers have high levels of zinc oxide causing severe inflammation in the surrounding tissue. Others do not flow well into canal irregularities.

With most root canal sealers, inflammatory reactions also occur due to spaces within the canal that are created as the root canal sealer is resorbed and dissolved in tissue fluid. Thus if the sealer is not sufficiently antimicrobial, when the sealer material disintegrates and the particles are removed from the canal by phagocytes, voids are left. These voids provide places for infection and inflammation to occur, which leads to eventual failure of the root canal. It may take anywhere from 6 months to 2 years for the failure to occur. The presence of an antimicrobial component could prevent this failure.

An ideal root canal sealer would exhibit the following characteristics: antimicrobial capacity; relatively non-irritating and non-inflammatory; adequate working time before setting; effectively seal both the apical and coronal ends of the root canal; and flow into canal irregularities.

Therefore, there is a need for a less-inflammatory root canal sealer that has a high level of antimicrobial effect in the canal with an adequate working time for the dentist.

SUMMARY

The present invention is directed to a root canal sealer formula which satisfies the above needs. The root canal sealer comprises the following powders in the following ratios: 31 to 41% zinc oxide; 25% staybelite resin; 10% bismuth subcarbonate; 10% barium sulphate; 1% anhydrous sodium borate; and 5-15% triiodomethane. The powders are mixed with 100% eugenol to form a creamy paste.

OBJECTS OF THE INVENTION

It is therefore an object of this invention to provide for a root canal sealer which has antimicrobial properties.

It is another object of this invention to provide for a root canal sealer which is less inflammatory than present formulations.

It is a further object of this invention to provide for a root canal sealer which has a lower concentration of zinc oxide.

It is a further object of this invention to provide for a root canal sealer which uses triiodomethane as an antimicrobial agent.

It is still a further object of this invention to improve the set time of the sealer.

It is still a further object of this invention to provide for an antimicrobial root canal sealer with an antimicrobial agent which is also radiopaque.

It is yet another object of this invention to provide for an antimicrobial root canal sealer to prevent inflammation, infection and failure of root canals.

DETAILED DESCRIPTION OF THE PREFERRED EMBODIMENT

This invention provides for a new and unique antimicrobial root canal sealer formulation which is more biocompatible, has improved and superior antimicrobial effects, longer setting time, improved radiopacity, and low solubility.

The new formulation employs triiodomethane, also known as iodoform, as a component of root canal sealer powder mixture and replaces some of the zinc oxide powder. This reduces the amount of zinc oxide and accordingly reduces the inflammatory potential of the resorbed zinc oxide particles. Moreover, iodoform has antibacterial properties as well as extremely low tissue toxicity.

Iodoform has been used in wounds and in extracted teeth sockets to reduce bacterial levels and help form healthy granulation tissue for repair. The use of iodoform as a root canal antiseptic goes back to 1913. However histologic studies have shown that it creates a severe inflammatory reaction in tissue within 2–4 days. It is the purpose of this new root canal sealer formulation to eliminate the severe inflammatory reaction associated with iodoform yet utilize the free iodine released as a long lasting antimicrobial.

The new root canal sealer formula which reduces the inflammatory reaction and provides excellent infection protection is as follows:

| CHEMICAL | PERCENT BY WEIGHT |
| --- | --- |
| zinc oxide | 31–41% |
| hydrogenated rosin glycerol ester (staybelite resin) | 25% |
| bismuth subcarbonate | 10% |
| barium sulphate | 10% |
| sodium borate (anhydrous) | 1% |
| triiodomethane | 5–15% |

The above components are combined in powder form and are mixed with 100% eugenol to form a creamy paste. The new sealer with iodoform is used in the same manner as the ones available without iodoform. It is inserted into the root canal and the gutta percha cone is pressed in over the sealant.

The root canal sealer is resorbed by the inflammatory tissue fluid which is highly acidic. Iodoform is most effective in an acidic environment as the free iodine radical is gradually released from the iodoform. It is this free iodine radical that has the antimicrobial properties. The free radical iodine is also less reactive chemically, therefore the inflammatory reaction normally occurring in the presence of iodoform is greatly reduced making it a more effective antibacterial agent.

The free iodine in tissue fluid is slowly liberated, creating an excellent reservoir of an antibacterial agent within the root canal system. In this respect, the iodine acts as a tripwire or an alarm for root canals that are beginning to breakdown due to obturation failure.

It is required that at least 5–15% of the root canal sealer powder mixture be iodoform. The iodine provides the antimicrobial agent which is missing from the zinc oxide sealers currently available. However, iodoform requires tissue fluid to activate it.

If the root canal is not failing, then no iodine free radical is released, but, when a root canal is failing due to resorption, that is the key time for the sealer material to guard against bacterial breakdown.

The set time of this new formulation is about six hours. This allows for an all day mix in an endodontist's office, instead of the usual mixes every half hour. Thus this new formulation is a more cost-effective sealer. Within the canal, it has been shown to set within 30 minutes, allowing sufficient working time for the operator. This setting time is enhanced due to canal moisture and humidity within the canal as well as body temperature.

Iodoform will have an antimicrobial action during the setting time after it has been inserted into the root canal. It is particularly effective against *S. aureus* which has been shown to be the post treatment bacteria left after the root canal is performed. Iodoform is also effective against various fungi, viruses, *E. Coli* and *P. aeroginosa*.

Iodoform is radiopaque, allowing for easy x-ray identification of sealer placement within the root canal. Therefore the necessity for a barium sulphate radiopacifier is reduced. Some of the barium sulphate is replaced with iodoform, a dual characteristic chemical that is both antibacterial and radiopaque.

Finally, triiodomethane has been shown to aid in cellular development by stimulating completion of root formation in infected cases of incomplete root development. Therefore, a root canal sealer formula which includes triiodomethane as one of its components acts to: prevent root canal failure because it is antimicrobial; reduce inflammation from zinc oxide by reducing the amount of zinc oxide; allow for longer set and working times; replace some of the radiopacifier component; and increase the prognosis and success rate of root canal treatments.

It is understood that the above description is meant to be illustrative only. Minor variations in the root canal sealer formula may be made without reducing the effectiveness of the root canal sealer and therefore departing from the intended scope of the claims.

What is claimed is:

1. A root canal sealer, comprising:

15.5–20.5 weight % zinc oxide;

12.5 weight. % hydrogenated rosin glycerol ester (staybelite resin);

5 weight % bismuth subcarbonate 5 weight % radiopague agent consisting of barium sulfate;

0.5% weight % anhydrous sodium borate;

2.5–7.5 weight % antimicrobial agent consisting of tri-iodomethane; and mixed with 50 weight % eugenol.

\* \* \* \* \*